United States Patent [19]

Carette et al.

[11] Patent Number: 5,124,456
[45] Date of Patent: Jun. 23, 1992

[54] HINDERED AMINE-SUBSTITUTED DIHYDROPYRIDINES AND HEAT/LIGHT STABILIZATION OF POLYMER SUBSTRATES THEREWITH

[75] Inventors: Louis Carette, Issy Les Moulineaux; Michel Gay, Villeurbanne; Sylvie Lavault, Lyon; Gilles Mur, Villeneuve Saint Georges, all of France

[73] Assignee: Rhone-Poulenc Chimie, Courbevoie, France

[21] Appl. No.: 591,826

[22] Filed: Oct. 2, 1990

[30] Foreign Application Priority Data

Oct. 2, 1989 [FR] France ................. 89/13053

[51] Int. Cl.$^5$ ........................... C07D 211/80
[52] U.S. Cl. ................ 546/193; 546/194; 546/321
[58] Field of Search ............ 546/194, 193, 321

[56] References Cited

U.S. PATENT DOCUMENTS 4,064,102 12/1977 Hillard et al. ................. 546/184
4,450,248 5/1984 Leistner et al. ................. 546/187
4,548,973 10/1985 Raynor ........................ 546/193

OTHER PUBLICATIONS

Schoenaginger et al., "Substituted, 1,4-dihydropyridines . . ." CA 102:9550r (1985).
Prostakov et al., "1,2,5-trimethyl . . ." CA 68:104915x (1968).

Primary Examiner—C. Warren Ivy
Assistant Examiner—Celia Chang
Attorney, Agent, or Firm—Burns, Doane, Swecker & Mathis

[57] ABSTRACT

Novel dihydropyridine compounds bearing substituted piperidyl substituents are effective heat/light stabilizers for a wide variety of polymer substrates, e.g., for halopolymers such as PVC, and are also effective anti-UV agents and antioxidants for such polymers as polyolefins, polystyrenes, polyalkadienes, polyurethanes, polyamides, polyesters, polycarbonates, polysulfones, polyethersulfones, polyetherketones, acrylic polymers, or copolymers or mixtures thereof.

14 Claims, No Drawings

HINDERED AMINE-SUBSTITUTED DIHYDROPYRIDINES AND HEAT/LIGHT STABILIZATION OF POLYMER SUBSTRATES THEREWITH

BACKGROUND OF THE INVENTION

1. Field of the Invention

The present invention relates to novel compounds comprising a dihydropyridine basic nucleus and bearing substituted piperidyl substituents.

This invention also relates to the use of such novel compounds for the heat and light stabilization of polymers.

2. Description of the Prior Art

FR-A-2,239,496 describes 2,6-dimethyl-3,5-dicarboxylate-1,4-dihydropyridines as heat stabilizers for polyvinyl chloride (PVC).

EP-A-0,005,678 describes the synergistic effect between 2,6-dimethyl-3,5-dicarboxylate-1,4-dihydropyridines and β-diketones for the heat stabilization of PVC.

These 1,4-dihydropyridine compounds are effective heat stabilizers for PVC. However, they are insufficient for certain applications where the polymer is subjected to external exposures, namely, in the event that the polymer must also have a stability to light.

SUMMARY OF THE INVENTION

Accordingly, a major object of the present invention is the provision of novel compounds adapted for the heat and light stabilization of polymers, said novel compounds comprising a 1,4-dihydropyridine basic nucleus and having one of the general formulae (Ia) or (Ib):

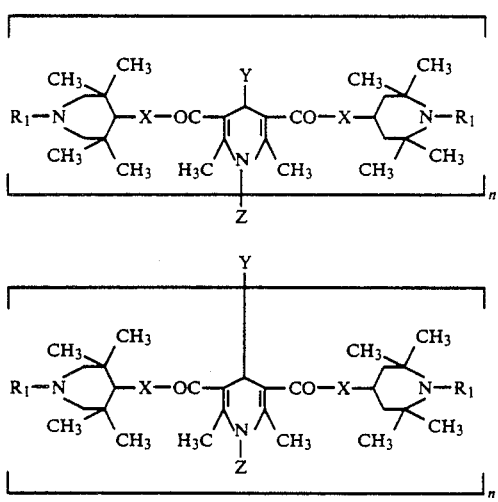

in which n is 1 or 2; $R_1$ is a hydrogen atom, a methyl radical or an acetyl radical; X is an oxygen atom, or an N-$R_2$ radical wherein $R_2$ is a hydrogen atom or an alkyl radical having from 1 to 18 carbon atoms; Y is a hydrogen atom, an alkyl radical having from 1 to 18 carbon atoms or a phenyl radical; Z is a hydrogen atom or an alkyl radical having from 1 to 18 carbon atoms; with the proviso that, when n=2, one of the two symbols Y and Z may be an alkylene radical having from 1 to 12 carbon atoms.

DETAILED DESCRIPTION OF THE PREFERRED EMBODIMENTS OF THE INVENTION

More particularly according to the present invention, the compounds of formulae (Ia) and (Ib) are advantageously prepared especially via Hantzsch's method [*Chemical Reviews*, 72, 1 (1972)] by reacting an acetoacetic ester or an acetoacetamide of formula (II):

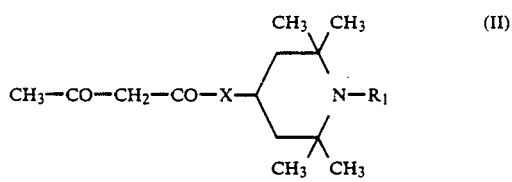

with an aldehyde of formula (III) Y—(—CHO)$_n$ and an amine of formula (IV) Z—(—NH$_2$)$_n$, wherein the various symbols n, X, $R_1$, Y and Z in the formulae (II), (III) and (IV) have the definitions given above in respect of the formulae (Ia) and (Ib).

Also, the operating technique described in *Organic Syntheses*, volume XIV, page 30 (1934) may be employed.

When each of X and Z simultaneously is a hydrogen atom, it is often simpler to use hexamethylenetetramine rather than the formaldehyde/ammonia mixture.

One operating technique for this alternative methodology is described in SU 300,465.

The acetoacetic esters and the acetamides of formula (II) themselves can be prepared by reacting diketene with 4-hydroxypiperidine or the corresponding 4-aminopiperidine of the formula (V):

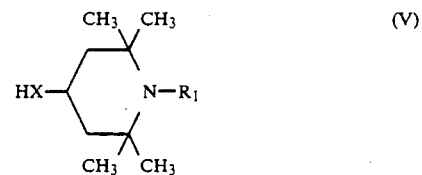

in which X is an oxygen atom of an -N-$R_2$ radical, with $R_1$ and $R_2$ having the definitions given above in respect of the compounds of formulae (Ia) and (Ib).

Exemplary of the compounds of formulae (Ia) or (Ib), particularly representative are:

2,6-Dimethyl-3,5-bis[(1,2,2,6,6-pentamethyl-4-piperidyl)oxycarbonyl]-1,4-dihydropyridine;

2,6-Dimethyl-3,5-bis[(2,2,6,6-tetramethyl-4-piperidyl)oxycarbonyl]-1,4-dihydropyridine;

2,6-Dimethyl-3,5-bis[(2,2,6,6-tetramethyl-4-piperidyl)aminocarbonyl]-1,4-dihydropyridine;

2,6-Dimethyl-3,5-bis[(2,2,6,6-tetramethyl-4-piperidyl)-N-butylaminocarbonyl]-1,4-dihydropyridine;

1,6-Bis[2,6-dimethyl-3,5-bis[(1,2,2,6,6-pentamethyl-4-piperidyl)oxycarbonyl]-1,4-dihydro-4-pyridyl]hexane.

The compounds of formulae (Ia) and (Ib) are useful as light stabilizers and heat stabilizers for organic polymers.

Thus, they can be incorporated as anti-UV agents in polyolefins, polystyrenes, polyalkadienes, polyurethanes, polyamides, polyesters, polycarbonates, polysulfones, polyethersulfones, polyetherketones, acrylic polymers, halogenated polymers, their copolymers and mixtures thereof.

The compounds of formula (I) are more particularly incorporated into polyolefins and polyalkadienes such as polypropylene, high density polyethylene, low density polyethylene, linear low density polyethylene, polybutadiene, their copolymers or mixtures thereof.

Thus, the present invention also features compositions of an organic polymer stabilized against the detrimental effects of light and ultraviolet rays by having incorporated therein an stabilizing amount of at least one compound of formulae (Ia) or (Ib).

These compositions characteristically contain from 0.004 to 20 milliequivalents of 2,2,6,6-tetramethylpiperidyl functional group per 100 g of polymer.

The stabilized polymeric compositions according to the invention preferably contain from 0.020 to 4 milliequivalents of 2,2,6,6-tetramethylpiperidyl functional goup per 100 g of polymer.

For example, the stabilized polymeric compositions of this invention advantageously contain from 0.01% to 5% by weight of at least one compound of formulae (Ia) or (Ib).

The addition or incorporation of the compounds of formulae (Ia) or (Ib) may be carried out either during or after the preparation of the polymers.

These organic polymer compositions containing the compounds of formulae (Ia) or (Ib) may additionally contain the other additives, adjuvants and stabilizers which are typically employed in this art, such as:

(i) Antioxidants, such as alkylated monophenols, alkylated hydroquinones, hydroxylated diphenyl sulfides, alkylidenebisphenols, benzyl compounds, acylaminophenols, esters of 3-(3,5-di-tert-butyl-4-hydroxyphenyl)-propionic acid, esters of 3-(5-tert-butyl-4-hydroxy-3-methylphenyl)propionic acid, esters of 3-(3,5-dicyclohexyl-4-hydroxyphenyl)propionic acid and amides of 3-(3,5-di-tert-butyl-4-hydroxyphenyl)propionic acid;

(ii) Absorbers of ultraviolet rays and light stabilizers such as 2-(2'-hydroxyphenyl)benzotriazoles, 2-hydroxybenzophenones, optionally substituted benzoic acid esters, acrylic esters, nickel compounds and oxalamides;

(iii) Metal-deactivators;
(iv) Phosphites and phosphonites;
(v) Peroxide-destroying compounds;
(vi) Nucleating agents;
(vii) Fillers and reinforcing agents;
(viii) Plasticizers;
(ix) Lubricants;
(x) Emulsifiers;
(xi) Pigments;
(xii) Optical whiteners;
(xiii) Flame retardants;
(xiv) Antistatics;
(xv) Blowing agents.

The stabilized polymer compositions may be used in the most diverse forms, for example in the form of molded objects, sheets, fibers, cellular materials (masses), profiles or coating products, or as film-formers (binders) for paints, varnishes, adhesives or cements.

The compounds of formulae (Ia) and (Ib) are also suitable as heat stabilizers, especially for the chlorinated polymers.

In particular, in such polymers they therefore serve as both UV stabilizers and heat stabilizers.

They can be employed by themselves, or in combination with other heat stabilizers such as, for example, organic tin derivatives.

In chlorinated polymers, the compounds of formulae (Ia) and (Ib) are also often used in combination with primary heat stabilizers.

These primary stabilizers are preferably organic derivatives of zinc, calcium, barium, magnesium and strontium and, where appropriate, hydrotalcites.

Thus, the present invention also features compositions based on a stabilized chlorinated polymer, comprising:

(a) an effective stabilizing amount of at least one organic zinc compound;

(b) an effective stabilizing amount of at least one organic compound of calcium, barium, magnesium or strontium and/or of a hydrotalcite;

(c) an effective stabilizing amount of at least one compound which comprises a 1,4-dihydropyridine functional group and having the formulae (Ia) or (Ib).

Especially representative chlorinated polymers are polyvinyl chloride (PVC), polyvinylidene chloride, the copolymers predominantly comprised of vinyl chloride recurring units prepared from vinyl chloride and other monomers, and mixtures of polymers of copolymers in which a predominant fraction is prepared from vinyl chloride.

Any type of PVC is generally suitable, whatever its method of preparation: polymerization in bulk, in suspension, in dispersion or of any other type, and whatever its intrinsic viscosity.

The vinyl chloride homopolymers may also be modified chemically, for example by chlorination.

Many vinyl chloride copolymers can also be stabilized against the effects of heat and light, namely, against yellowing and degradation. These are, in particular, the copolymers prepared by copolymerization of vinyl chloride with other monomers containing a polymerizable ethylenic bond, such as, for example, vinyl acetate or vinylidene chloride, maleic or fumaric acids or their esters, olefins such as ethylene, propylene or hexene, acrylic or methacrylic esters, styrene, and vinyl ethers such as vinyl dodecyl ether.

These copolymers usually contain at least 50% by weight of vinyl chloride recurring units and preferably at least 80% by weight of vinyl chloride recurring units.

The compositions according to the invention may also contain mixtures based on chlorinated polymers containing minor amounts of other polymers, such as halogenated polyolefins or acrylonitrile/butaiene/styrene copolymers.

PVC by itself or mixed with other polymers is the chlorinated polymer most widely employed in the compositions of the invention.

The organic zinc compounds are preferably zinc carboxylates and phenolates.

Those most commonly employed are, for example, the zinc salts of maleic, acetic, diacetic, propionic, hexanoic, 2-ethylhexanoic, decanoic, undecanoic, lauric myristic, palmitic, stearic, oleic, ricinoleic, behenic, hydroxystearic, hydroxyundecanoic, benzoic, phenylacetic, para-tert-butylbenzoic and salicylic acids, and zinc phenolates of phenol and of phenols substituted by one or more alkyl radicals, such as nonylphenols.

For practical reasons or for economic reasons, the organic zinc compounds which are preferably selected from among those indicated above are zinc propionate, zinc 2-ethylhexanoate, zinc lauratic, zinc stearate, zinc oleate, zinc ricinoleate, zinc benzoate, zinc para-tertbutylbenzoate, zinc salicylate, zinc mono(2-ethylhexyl) maleate and zinc nonylphenates.

The organic zinc compounds are typically incorporated in an amount ranging from 0.005% to 1% by weight relative to the weight of the chlorinated polymer, and preferably from 0.01% to 0.6% by weight.

The organic calcium, barium, magnesium and strontium compounds are preferably the carboxylates and phenolates of these metals.

Those most typically incorporated are, for example, the calcium, barium, magnesium and strontium salts of maleic, acetic, diacetic, propionic, hexanoic, 2-ethylhexanoic, decanoic, undecanoic, lauric, myristic, palmitic, stearic, oleic, ricinoleic, behenic, hydroxystearic, hydroxyundecanoic, benzoic, phenylacetic, para-tert-butylbenzoic and salicylic acids, the calcium, barium, magnesium and strontium phenolates of phenol and of phenols substituted by one or more alkyl radicals, such as nonylphenols.

For practical reasons or for economic reasons, the organic calcium, barium, magnesium and strontium compounds referred to above which are the preferred are the calcium, barium and magnesium salts of propionic, 2-ethylhexanoic, lauric, stearic, oleic, ricinoleic, benzoic, para-tert-butylbenzoic and salicylic acids and of mono(2-ethylhexyl)maleate, as well as calcium, barium and magnesium nonylphenates.

The organic compounds of calcium, barium, magnesium and strontium or the hydrotalcites are typically incorporated in an amount ranging from 0.005% to 5% by weight relative to the weight of the chlorinated polymer, and preferably from 0.02% to 2% by weight.

Organic calcium compounds or mixtures of organic calcium compounds and organic magnesium compounds will advantageously be employed for food-contact applications and especially for PVC bottles.

The hydrotalcites which may be introduced into the compositions based on a chlorinated polymer according to the invention, whether instead of the organic calcium, barium, magnesium and strontium compounds or in combination with such compounds, are especially those compounds described in French Patent FR-A-2,483,934 and in European Patent EP-A-0,063,180.

The compositions based on the chlorinated polymer typically contain from 0.005% to 5% by weight of the compound of formulae (Ia) or (Ib) relative to the weight of the chlorinated polymer.

They preferably contain from 0.01% to 2% by weight of compound of formulae (Ia) or (Ib) relative to the chlorinated polymer.

When compared with the 1,4-dihydropyridines of the prior art which have heretofore been employed as heat stabilizers for chlorinated polymers, the compounds of formula (I) exhibit at least the same efficiency in terms of the resistance to yellowing at the same weight, namely, for a smaller amount of 1,4-dihydropyridine units, but additionally provide an effective protective action against UV radiation.

It will of course be appreciated that it is also possible to introduce other additives into the compositions based on chlorinated polymers of the invention.

Thus, this is especially the case with β-diketones or β-ketoaldehydes, which exhibit synergistic effect with the compounds containing a dihydropyridine functional group.

These β-diketones are particularly described in French Patents and Certificates of Addition Nos. FR 2,292,227, FR 2,324,681, FR 2,351,149, FR 2,352,025, FR 2,383,988 and FR 2,456,132 and in European Patents EP 0,040,286 and EP 0,046,161.

Exemplary such β-diketones are benzoylstearoylmethane, dibenzoylmethane, benzoylacetone, benzoyl-3-methylbutanoylmethane, methoxycarbonylbenzoylbenzoylmethanes, and bis-β-diketones such as 1,4-bis(acetylaceto)butane, 1,8-bis(benzoylaceto)octane and 1,4-bis(acetylaceto)benzene.

When present, the β-diketones are incorporated in an amount ranging from 0.005% to 5% by weight relative to the weight of the chlorinated polymer and preferably from 0.01% to 2% by weight.

The compositions of the invention may also contain other secondary heat stabilizers such as polyols, phosphites or epoxy compounds.

The polyols generally present the advantage of lengthening the useful lives of the chlorinated polymers subjected to a heat treatment.

It is generally preferable that the polyols employed should have a boiling point higher than 150° C. and preferably higher than 170° C., because of the use of the chlorinated polymers at elevated temperature.

Exemplary such polyols include triols such as trimethylolpropane, glycerol, 1,2,6-hexanetriol, 1,2,4-butanetriol or trishydroxyethyl isocyanurate, tetrols such as pentaerythritol or diglycerol, pentitols such as xylitol or tetramethylolcyclohexanol, hexitols such as mannitol, sorbitol or dipentaerythritol, polyols which are partially esterified with a carboxylic acid and which comprise at least 3 free hydroxyl functional groups, polyvinyl alcohols, especially those in which there remains less than 30 mol% of ester groups relative to the combination of their ester and hydroxyl groups and which have a viscosity ranging from about $4 \times 10^{-3}$ Pa.s to $60 \times 10^{-3}$ Pa.s at 20° C. in an aqueous solution at a concentration of 4% by weight.

Among such polyols, those preferred are xylitol, mannitol, sorbitol, tetramethylolcyclohexanol and polyvinyl alcohols indicated above.

When present in the compositions according to the invention, from 0.005% to 1% by weight of polyol relative to the weight of the chlorinated polymer, and preferably from 0.01% to 0.6% by weight, is typically incorporated.

The epoxides which may be incorporated into the compositions according to the invention are generally complex compounds, usually epoxidized polyglycerides such as epoxidized soya oil, which is that most frequently employed, epoxidized linseed oil, epoxidized fish oils and epoxidized tall oil.

The compositions according to the invention may also contain organic phosphites, especially aliphatic phosphites or aromatic phosphites, or mixed aliphatic and aromatic phosphites.

Particularly exemplary such phosphites include:
Pentaerythrityl dialkyl diphosphites;
Pentaerythrityl diphenyl diphosphites;
Pentaerythrityl 2,4-bis(di-tert-butylphenyl) diphosphites;
Tetraalkyl bis(1,4-phenylene)dimethylmethane diphosphites;
Tetraalkyl bis(2,5-dialkyl-1,4-phenylene)alkylmethanediphosphites;
Diphenyl bis[2-(2-butoxyethoxy)ethyl] 4,4'-isopropylidenediphenyl diphospite;
Tetrakis[2-(2-butoxyethoxy)ethyl] 4,4'-isopropylidenediphenyl diphosphite;
Diphenyl tris[2-(2-butoxyethoxy)ethyl] bis(4,4'-isopropylidenediphenyl) triphosphite;

Diphenyl tetrakis[2-(2-butoxyethoxy)ethyl] tris-(4,4'-isopropylidenediphenyl) tetraphosphite;
Diphenyl bis[2-(2-butoxyethoxy)ethyl] 4,4'-isopropylidenediphenyl diphospite;
Tetrakis[2-(2-butoxyethoxy)ethyl] 4,4'-isopropylidenediphenyl diphosphite;
Diphenyl tris[2-(2-butoxyethoxy)ethyl] bis(4,4'-isopropylidenediphenyl) triphosphite;
Diphenyl tetrakis[2-(2-butoxyethoxy)ethyl] tris(4,4'-isopropylidenediphenyl) tetraphosphite;
Diphenyl pentakis[2-(2-butoxyethoxy)ethyl] tetrakis(4,4'-isopropylidenediphenyl) pentaphosphite;
Diphenylhexakis[2-(2-butoxyethoxy)ethyl] pentakis(4,4'-isopropylidenediphenyl) hexaphosphite;
Pentakis[2-(2-butoxyethoxy)ethyl] bis(4,4'-isopropylidenediphenyl) triphosphite;
Hexakis[2-(2-butoxyethoxy)ethyl] tris(4,4'-isopropylidenediphenyl) tetraphosphite;
Bis(2,4-di-tert-butylphenyl) bis[2,(2-butoxy-ethoxy)ethyl]4,4'-isopropylidenediphenyl diphosphite; and
Bis(2,6-di-tert-butylphenyl) bis[2-(2-butoxyethoxy)ethyl]4,4'-isopropylidenediphenyl diphosphite.

When present, the phosphite generally constitutes from 0.05% to 5% by weight relative to the weight of the chlorinated polymer, and preferably from 0.1% to 2% by weight.

The compositions according to the invention may also contain the usual adjuvants such as phenolic antioxidants and anti-UV agents such as benzophenones or benzotriazoles.

The compositions of the invention may be rigid formulations, i.e., devoid of plasticizer, or semirigid, i.e., having low plasticizer contents, such as for applications in the construction industry or for bottle manufacture. However, the compositions of the invention may also be employed in plasticized formulations, such as for the manufacture of films for agricultural use.

The incorporation of the various stabilizers or adjuvants is typically carried out using the chlorinated polymer in the form of powder.

It is possible, of course, to prepare a mixture of two or more of the constituents of the compositions according to the invention before they are incorporated into the chlorinated polymer.

All of the usual methods for incorporating the various stabilizers or adjuvants in the polymer can be employed. For example, the homogenization of the polymeric composition can be carried out in a blender or on a roll mill, at a temperature such that the composition becomes fluid, normally ranging from 150° C. to 200° C. in the case of PVC, and for a sufficient period of time, on the order of a few minutes to a few tens of minutes.

The chlorinated polymer compositions and more particularly PVC can be processed according to all of the techniques usually employed in this art, such as, for example, extrusion, injection, blow-extrusion, calendering or rotational molding.

Among the compounds of formula (Ib), the compounds of the general formula (VI):

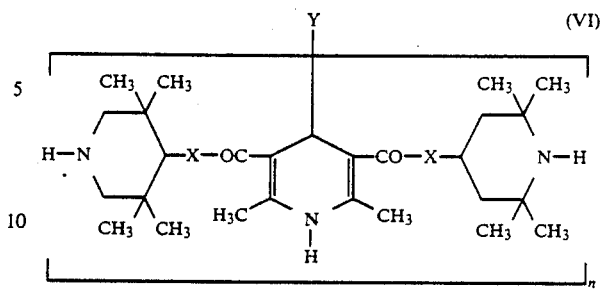

in which n is 1 or 2; X is an oxygen atom or an $N—R_2$ radical wherein $R_2$ is a hydrogen atom or an alkyl radical having from 1 to 18 carbon atoms; Y is a hydrogen atom, an alkyl radical having from 1 to 18 carbon atoms or a phenyl radical; with the proviso that, when $n=2$, Y is a linear or branched chain alkylene radical having from 1 to 12 carbon atoms; are particularly effective as antioxidants in the organic polymers indicated above, more particularly in the polyolefins, polystyrenes, polyalkadienes, polyurethanes, polyamides, polyesters, polycarbonates, polysulfones, polyethersulfones, polyetherketones, acrylic polymers, halogenated polymers, copolymers and mixtures of these polymers.

Among the above organic polymers, the antioxidant activity of the compounds of general formula (VI) is more particularly useful in the case of polyolefins such as low density polyethylene, linear low density polyethylene, high density polyethylene and polypropylene, polystyrenes, polyalkadienes, polyamides, polyesters and polyurethanes.

For such antioxidant function, from 0.01% to 5% by weight of compound of formula (VI) is typically incorporated relative to the weight of polymer to be stabilized, and preferably from 0.05% to 2% by weight per weight.

It has also been determined that the compounds of formula (VI) provide a beneficial effect from the standpoint of what is generally referred to as "processing", namely, essentially during the conversion of the polymer with heating.

It is noted that the polymer containing one or more compounds of formula (VI) exhibits no (or little) degradation or crosslinking during its processing with heating, in contrast to the polymer by itself or to the polymer containing a known compound including a hindered amine group, or a known compound with a dihydropyridine functional group, or a mixture of compounds of these two types. This is especially the case in respect of the polyolefins and more especially with polypropylene.

The polymeric compositions containing one or more compounds of formula (VI) may, of course, contain the usual adjuvants for a composition of this type, as indicated above.

Indeed, except for the more specific selection of the compounds of formula (VI) when it is desired to provide polymeric compositions which are more resistant to oxidation and more stable when processed, the polymeric compositions of the invention include adjuvants of the same types because, for effective use thereof, a composition must be stabilized against the various categories of degradation: oxidation, heat, light, etc.

Further in connection with their use as antioxidants, the compounds of formula (VI) are especially useful in combination with certain organic phosphites such as, particularly, tris(2,4-di-tert-butylphenyl) phosphite.

In order to further illustrate the present invention and the advantages thereof, the following specific examples are given, it being understood that same are intended only as illustrative and in nowise limitative.

EXAMPLE 1

Preparation of 2,6-dimethyl-3,5-bis-[(2,2,6,6-tetramethyl-4-piperidyl)-oxycarbonyl]-1,4-dihydropyridine (1a) Preparation of 4-acetoacetoxy-2,2,6,6-tetramethylpiperidine Into a 500-cm$^3$ three-necked round bottom flask fitted with a central stirrer, with a thermometer pocket, a reflux condenser and a dropping funnel, were charged:

(i) 31.4 g (0.2 mol) of 4-hydroxy-2,2,6,6tetramethylpiperidine;

(ii) 200 cm$^3$ of toluene;

(iii) 1 cm$^3$ of triethylamine (catalyst).

The contents were heated to 70° C. with stirring and 16.8 g (0.2 mol) of diketene were then steadily introduced over 30 min., while the temperature was maintained at 70° C.

This temperature was maintained for another 2 h, 30 min, upon completion of the addition.

All of the above were carried out under nitrogen atmosphere.

The toluene, the triethylamine and the trace amounts of diketene were then removed under reduced pressure by progressive heating:

(a) pressure of 2,000 Pa progressively decreased to 65 Pa, (b) temperature of 20° C. increased to 65° C. at the end of operation.

48.1 g of a homogeneous, orangy-yellow oil were thus obtained, analyzing by acidimetry at 393 milliequivalents (meq) of β-ketoester functional group per 100 g (theory: 414.9 meq/100 g), which corresponded to a purity of approximately 95%.

The unexpected structure was confirmed by its infrared spectrum and its mass spectrum.

(1b) Preparation of 2,6-dimethyl-3,5-bis-[(2,2,6,6,-tetramethyl-4-piperidyl)-oxycarbonyl]-1,4-dihydropyridine:

Into the apparatus described in Example (1a) were charged:

(i) 4-acetoacetoxy-2,2,6,6-tetramethylpiperidine prepared in (1a) (95% pure): 38.05 g (0.15 mol);

(ii) hexamethylenetetramine: 2.00 g (0.014 mol);

(iii) ammonium acetate: 4.95 g (0.0643 mol);

(iv) isopropanol containing 20% of water by volume: 100 cm$^3$.

The homogeneous reaction mixture was stirred and heated to about 72° C. under nitrogen atmosphere for 2 h, 50 min.

After cooling, the pH of the mixture was adjusted to 11.4 by addition of a 5 N sodium hydroxide solution. 700 cm$^3$ of water were then added with vigorous stirring; a precipitate was formed and was filtered off, washed with water and dried at 80° C. under reduced pressure.

This yielded 26.8 g of a practically pure yellow solid which had a melting point of 189°-190° C., and whose infrared and mass spectra were consistent with the expected structure.

The yield of isolated pure product was 75% relative to the compound (1a) introduced.

EXAMPLE 2

(2a) Preparation of 4-acetoacetoxy-1,2,2,6,6-pentamethylpiperidine:

The procedure of Example (1a) was repeated using 4-hydroxy-2,2,6,6-tetramethyl-N-methylpiperidine.

An orangy-yellow oil was obtained, analyzing by acidimetry at 369 meq/100 g (theory: 392 meq/100 g): approximately 94% purity.

(2b) Preparation of 2,6-dimethyl-3,5-bis-[(1,2,2,6,6,-pentamethyl-4-piperidyl)-oxycarbonyl]-1,4-dihydropyridine:

The procedure of Example (1b) was repeated, the 4-acetoacetoxy-2,2,6,6-tetramethylpiperidine being replaced with the same molar amount of 4-acetoacetoxy-1,2,2,6,6-pentamethylpiperidine obtained in (2a).

2,6-Dimethyl-3,5-bis[(1,2,2,6,6-pentamethyl-4-piperidyl)oxycarbonyl]-1,4-dihydropyridine was obtained in the form of a yellow solid which had a melting point of 232° C. and whose infrared, nuclear magnetic resonance (NMR) and mass spectra were consistent with the structure.

EXAMPLE 3

(3a) Preparation of 4-acetoacetamido-2,2,6,6tetramethylpiperidine

The procedure of Example (1a) was repeated using 4-amino-2,2,6,6-tetramethylpiperidine, without introducing catalyst and performing the addition of diketene at a temperature of 0° C. to 10° C.; 4-acetoacetamido-2,2,6,6-tetramethyl-piperidine was obtained in the form of a white solid which had a melting point of 115° C.

The yield of pure isolated product relative to the 4-amino-2,2,6,6,-tetramethyl compound introduced was 90%.

(3b) Preparation of 2,6-dimethyl-3,5-bis-[(2,2,6,6-tetramethyl-4-piperidyl)-aminocarbonyl]-1,4-dihydropyridine:

Into a 100-cm$^3$ conical flask were charged:

(i) 1.50 g (0.050 mol) of formaldehyde;

(ii) 21.3 g (0.089 mol) of 4-acetoacetamido-2,2,6,6-tetramethylpiperidine prepared in (3a);

(iii) 20 cm$^3$ of absolute ethanol;

(iv) 5 drops of diethylamine.

The homogeneous reaction mixture thus obtained was permitted to stand at 4° C. for 24 hours and then at room temperature for 48 h.

4.6 cm$^3$ of an ammoniacal aqueous solution containing 290 g/liter of NH$_3$ (i.e., 0.078 mol of NH$_3$) were then added.

The materials were heated to 75°-80° C. for 5 hours and were then maintained at room temperature for 24 hours.

After distillation of the solvents under reduced pressure, 23 g of a slightly pasty orangy solid were obtained.

This solid was dissolved in 200 cm$^3$ of methanol and was then precipitated by addition of 500 cm$^3$ of water with vigorous stirring.

The precipitate obtained was filtered off, washed with water and dried at 40° C. under reduced pressure.

This yielded 4.5 g of a yellow solid which had a melting point of 170° C. and whose structure was confirmed by NMR as 2,6-dimethyl-3,5-bis[(2,2,6,6-tetramethyl-4-piperidyl)aminocarbonyl]-1,4-dihydropyridine.

EXAMPLE 4

4(a) Preparation of 4-N-n-butylacetoacetamido-2,2,6,6-tetramethylpiperidine

The procedure of Example (3a) was repeated, but using 4-n-butylamino-2,2,6,6-tetramethylpiperidine. 4-N-n-butylacetoacetamido-2,2,6,6-tetramethylpiperidine was obtained in the form of a viscous yellow liquid greater than 95% purity.

4(b) Preparation of 2,6-dimethyl-3,5-bis-[(2,2,6,6,-tetramethyl-4-piperidyl)-n-butylaminocarbonyl]-1,4-dihydropyridine The procedure of Example 3(b) was repeated, using the compound prepared in (4a) instead of 4-acetoacetamido-2,2,6,6-tetramethylpiperidine.

2,6-Dimethyl-3,5-bis[[(2,2,6,6-tetramethyl-4-piperidyl)-n-butylaminocarbonyl]-1,4-dihydropyridine was obtained in the form if a white solid which had a melting point of 172° C. The infrared and mass spectra were consistent with the expected structure.

EXAMPLE 5

Preparation of 1,6-bis[2,6-dimethyl-3,5-bis[1,2,2,6,6-pentamethyl-4-piperidyl-oxycarbonyl]-1,4-dihydro-4-pyridyl]-hexane The procedure of (3b) was repeated, formaldehyde being replaced by 3.55 g (0.025 mol) of octanedial and introducing the 4-acetoacetoxy-1,2,2,6,6-pentamethyl-piperidine prepared in Example (2a).

This gave (in a 70% yield) 19.7 g of a yellow solid which had a melting point of approximately 110° C. and whose structure was confirmed by NMR.

EXAMPLES 6 to 11 and Comparative Tests A1 and A2

Heat Stabilization of PVC

The following base composition A was prepared:
(i) PVC powder prepared by suspension polymerization and marketed under the trademark Lacqvyl SO 71 S (viscosity index according to NF Standard T 51013:80):1,000 g
(ii) Impact modifier (butadiene/styrene/methyl methacrylate copolymer: 80 g
(iii) Lubricant based on rosin ester (wax E): 5 g
(iv) Epoxidized soya oil: 30 g
(v) Calcium stearate: 3 g
(vi) Zinc stearate: 2.5 g After homogenization in a fast blender, cold, 8 fractions of this composition A were withdrawn. To each fraction was added an amount of compound prepared in Example (2b) (DHP/HALS Ex. (2b)), in Example (1b) (DHP/HALS Ex. (1b)), in Example 5 (DHP/HALS Ex. 5) or of 2,6-dimethyl-3,5-bis(dodecyloxycarbonyl)-1,4-dihydropyridine (prior art DHP) and/or of stearoylbenzoylmethane (SBM). The amounts by weight per 100 g of PVC are reported in Table 1 below.

1-mm thick sheets were prepared from the various compositions thus obtained, and from the unmodified composition A, by blending on a 2-roll mill at 180° C. for 3 min.

Using test specimens (approximately 1 cm × 2 cm) cut from these sheets, a heat-aging test was carried out in a ventilated oven at 180° C. and the change in the Gardner color was monitored as a function of time.

The Gardner color values measured for various aging times up to 30 minutes are reported in Table 1.

TABLE I

| TESTS | STABILIZERS NATURE | Weight in g/100 g PVC | GARDNER VALUES AS A FUNCTION OF TIME IN MINUTES | | | | |
|---|---|---|---|---|---|---|---|
| | | | 0 | 7 | 14 | 21 | 30 |
| Control | none | — | 3 | 7 | 7 | 7 | 7 |
| Test A1 | DHP/prior art | 0.2 | 1 | 1.5 | 1.5 | 1.5 | 2.5 |
| Example 6 | DHP/HALS Example 2b | 0.2 | 0.5 | 1 | 1 | 1 | 2 |
| Example 7 | DHP/HALS Example 2b | 0.1 | 1 | 2 | 2 | 2 | 3 |
| Example 8 | DHP/HALS Example 2b | 0.3 | 0.5 | 1 | 1 | 1 | 2 |
| Test A2 | SBM | 0.3 | 0 | 0 | 1 | 1.5 | 2 |
| Example 9 | DHP/HALS Example 2b SBM | 0.1 0.2 | 0 | 0 | 0 | 0.5 | 1.5 |
| Test A3 | SBM DHP/prior art | 0.2 0.1 | 0 | 0 | 0 | 1 | 2 |
| Example 10 | DHP/HALS Example 1b | 0.2 | 0.5 | 1 | 1 | 1 | 2 |
| Example 11 | DHP/HALS Example 5 | 0.2 | 1 | 1.5 | 2 | 2 | 6 |

EXAMPLE 12 and Comparative Test B1

UV Stabilization of PVC

The following base composition B was prepared:
(i) Lacqvyl SO 71 S PVC: 1,000 g
(ii) Internal lubricant (mixture of hexadecanol and octadecanol): 14 g
(iii) Lubricant wax E (based on rosin ester): 2 g
(iv) Lubricant wax OP (based on partially saponified propylene glycol montanate): 3 g
(v) Thiotin stabilizer*: 15 g
(* mixture of 75% by weight of dioctylstanniobis-(isooctyl) sulfuroacetate), and of 25% by weight of isooctyl trioctylstanniosulfuroacetate).

After homogenization in a cold blender, two fractions of this composition B were withdrawn. To each fraction was added either 0.10 g (per 100 g of PVC) of compound of formula (Ia) or (Ib) prepared in Example (1b) (DHP/HALS Ex. (1b)), or 0.10 g (per 100 g of PVC) of an anti-UV agent generally employed in PVC (anti-UVP).

Sheets approximately 1 mm in thickness were prepared from these various compositions and with the composition B by itself, by blending on a 2-roll mill at 180° C. for 3 min.

These sheets were used to prepare 200-μm films using a press with platens heated to 185°.

These films were placed in an artificial accelerated aging chamber, at 30° C., equipped with a 40-W fluorescent tube of B type, emitting between 275 nm and 380 nm, with an intensity maximum at 310 nm.

The change in the optical density of the polyene sequences (containing 10 conjugated double bonds) was monitored in the visible spectrum at a wavelength λ=447 nm.

After 750 hours of aging, the values reported in Table II below were obtained.

TABLE II

| Tests | Anti-UV Stabilizers in g/100 g PVC | Optical density at $\lambda = 447$ nm after 750 hours' aging |
|---|---|---|
| Control | none | 0.18 |
| Example 12 | DHP/HALS Ex. 1B | 0.04 |
| Test B1 | Anti UVP* | 0.07 |

*Anti UVP = 2-hydroxy-4-octyloxybenzophenone (benzophenone-type anti-UV stabilizer very widely employed in PVC)

The very marked anti-UV effect of the compound of formula (Ia) and (Ib) prepared in Example (1b) was observed; this effectiveness was superior to that of a very widely employed anti-UV agent of benzophenone type. In addition, this effectiveness existed in a composition which was heat-stabilized with a thiotin compound, the photosensitizing effect of which is known and considerable.

EXAMPLE 13

Photostabilization of Appryl 3030 P polypropylene (PP) marketed by BP Chimie

Approximately 300 g of each of the mixtures whose weight composition is indicated in the following Table III were prepared in a slow blender:

TABLE III

| Composition | C | D | E | F | G | H | J | K | L | M |
|---|---|---|---|---|---|---|---|---|---|---|
| PP | 100 | 100 | 100 | 100 | 100 | 100 | 100 | 100 | 100 | 100 |
| Ca stearate | 0.1 | 0.1 | 0.1 | 0.1 | 0.1 | 0.1 | 0.1 | 0.1 | 0.1 | 0.1 |
| Phenolic antioxidant* | 0.02 | 0.02 | 0.02 | 0.02 | 0.02 | 0.02 | 0.02 | 0.02 | 0.02 | 0.02 |
| Chimassorb 944 commercial anti-UV** | 0 | 0 | 0.15 | 0 | 0 | 0 | 0 | 0.30 | 0 | 0 |
| Tinuvin 770 commercial HALS*** | 0 | 0.15 | 0 | 0 | 0 | 0 | 0.30 | 0 | 0 | 0 |
| HALS/DHP Example 1b | 0 | 0 | 0.15 | 0 | 0 | 0 | 0 | 0 | 0.30 | 0 |
| HALS/DHP Example 2b | 0 | 0 | 0 | 0 | 0.15 | 0 | 0 | 0 | 0 | 0.30 |
| HALS/DHP Example 5 | 0 | 0 | 0 | 0 | 0 | 0.15 | 0 | 0 | 0 | 0 |

*Pentaerythrityl 3-tetra(4-hydroxy-3,5-di-tert-butylphenyl)propionate
**Chimassorb 944

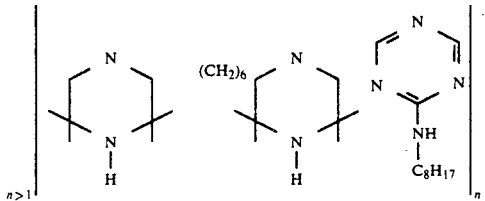

***Tinuvin 770: bis(2,2,6,6-tetramethyl-4-piperidyl)dodecanoate

These compositions were extruded under the following conditions:
(a) Thoret trademark extruder:
screw diameter = 20 mm
screw length = 400 mm
(b) Temperature profile:
zone 1 = 200° C.
zone 2 = 220° C.
zone 3 = 220° C.
zone 4 = 230° C.
die head = 215° C.

The lace obtained was granulated and the granules were then pressed into 200 μm films using a Carver press under the following conditions:
(a) Temperature = 210° C.
(b) Time = 5 min.
(c) Pressure = 20 MPa.

These films were exposed in an accelerated aging chamber of Sairem-Sepap 12-24 type. In this chamber, the samples were arranged on a cylindrical roundabout driven in a circular rotary movement. The roundabout itself was situated in the center of a parallelepipedal chamber whose 4 corners are occupied by a "medium pressure" mercury vapor lamp of Mazda MA 400 W type.

The lamp envelope only permitted radiation of wavelengths longer than 300 nm to pass (a device of this type is described in French Patent 2,430,609).

The temperature of the chamber was maintained at 60° C. by a control system.

The aging of the films was monitored by infrared spectrometry: the optical density of the carbonyl band at 1720–1740 cm$^{-1}$ reflected the degree of photooxidation of the polymeric material.

The results obtained are reported in Table IV below:

TABLE IV

| Composition | Anti-UV Stabilizer | Time to obtain an optical density of 0.3 |
|---|---|---|
| C | none | 35 h |
| D | Tinuvin 770 | 320 h |
| E | Chimmasorb 944 | 232 h |
| F | HALS/DHP Ex. 1b | 250 h |
| G | HALS/DHP Ex. 2b | 270 h |
| H | HALS/DHP Ex. 1b | 234 h |
| J | Tinuvin 770 | 600 h |
| K | Chimmasorb 944 | 400 h |
| L | HALS/DHP Ex. 1b | 450 h |
| M | HALS/DHP Ex. 2b | 400 h |

EXAMPLE 24

Photostabilization of Polypropylene 5 mixtures of the following powders were prepared separately:
(i) Neste polypropylene: 100 g
(ii) Irganox 1076 phenolic antioxidant*: 0.05 g
(iii) Calcium stearate: 0.10 g
(iv) Anti-UV to be tested: 0 or 0.15
(see Table V)

* Irganox 1076 = octadecyl 3-(4-hydroxy-3,5-di-tertbutylphenyl)propionate.

These various mixtures were homogenized dry in a slow blender for 5 minutes.

Sheets were then prepared by operating at 170° C. for 5 minutes in a 2-roll mill.

200-μm thick films were prepared from these sheets by pressing in a Schabentann press under the following conditions:

(a) Contact: 2 min. at 220° C.
(b) Pressing: 1 min. under 37 MPa (370 bars)

The films obtained were then placed in an artificial aging chamber equipped with 400-W fluorescent tubes of the B type: the spectrum was between 275 and 380 nm with a maximum at 310 nm. The temperature of the chamber was maintained at 55° C. in a moisture-saturated atmosphere.

As in the preceding example, the change in the optical density of the carbonyl band at 1720–1740 cm$^{-1}$, which reflected the degree of aging of the polymer, was monitored.

The following results were obtained (aging period required to obtain an optical density of 0.3).

TABLE V

| Anti-UV Stabilizer | | Time to obtain an optical density of 0.3 |
|---|---|---|
| Nature | Quantity g | |
| None | 0 | 40 h |
| Chimassorb 944 | 0.15 | 270 h |
| HALS/DHP Ex. 1b | 0.15 | 400 h |
| HALS/DHB Ex. 3b | 0.15 | 310 h |
| HALS/DHB Ex. 4b | 0.15 | 300 h |

EXAMPLE 15

Thermomechanical stabilization of VB 65 11 B polypropylene (PP) marketed by the Neste company Each of the mixtures whose weight composition is reported in the following Table VI was prepared in a fast blender:

TABLE VI

| Composition | N | P | Q | R | S | T | U |
|---|---|---|---|---|---|---|---|
| PP | 100 | 100 | 100 | 100 | 100 | 100 | 100 |
| Ca staerate | 0.1 | 0.1 | 0.1 | 0.1 | 0.1 | 0.1 | 0.1 |
| Irganox 1076* antioxidant | 0.05 | 0.05 | 0.05 | 0.05 | 0.05 | 0.05 | 0.05 |
| Tinuvin 622 commercial HALS** | 0 | 0 | 0.2 | 0 | 0 | 0.2 | 0 |
| Tinuvin 770 commercial HALS*** | 0 | 0.2 | 0 | 0 | 0.2 | 0 | 0 |
| Prior art DHP**** | 0 | 0 | 0 | 0.2 | 0.1 | 0.1 | 0 |
| HALS/DHP Example 1b | 0 | 0 | 0 | 0 | 0 | 0 | 0.1 |

*Irganox 1076 = octadecyl 3-(4-hydroxy-3,5-di-tert-butylphenyl)propionate
**Tinuvin 622 =

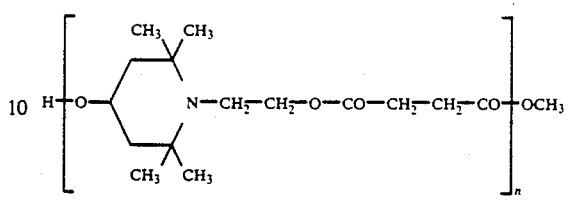

***Tinuvin 770 = see Example 13
****Prior art DHP = see Examples 6 to 11

The stabilization of the molten polymer was examined using a Brabender Plastograph.

The temperature of the kneading chamber was maintained at 220° C.

The torque exerted on the mixture was monitored over time.

The thermomechanical stability was evaluated as the ratio of the torque exerted on each of the mixtures N to U to the torque exerted on the mixture N, after 15 min. of application of the thermomechanical stress.

The higher this ratio, the better the thermomechanical stability.

The following Table VII reports the values of stability for the various compositions:

TABLE VII

| Composition | Stabilizer | Thermomechanical stability |
|---|---|---|
| N | none | 1 |
| P | Tinuvin 770 | 0.76 |
| Q | Tinuvin 622 | 0.95 |
| R | prior art DHP | 1.23 |
| S | Tinuvin 770 + DHP | 0.95 |
| T | Tinuvin 622 + DHP | 1.1 |
| U | HALS/DHP Ex. 1b | 2.18 |

EXAMPLE 16

Thermomechanical stabilization of VB 65 11 B polypropylene (PP) marketed by the Neste company The thermomechanical behavior of the compositions, indicated in Table VIII below, was measured under the conditions of Example 15.

TABLE VIII

| Composition | a | b | c | d | e | f | g | h | j | k | l | m | n |
|---|---|---|---|---|---|---|---|---|---|---|---|---|---|
| PP | 100 | 100 | 100 | 100 | 100 | 100 | 100 | 100 | 100 | 100 | 100 | 100 | 100 |
| Ca stearate | 0.1 | 0.1 | 0.1 | 0.1 | 0.1 | 0.1 | 0.1 | 0.1 | 0.1 | 0.1 | 0.1 | 0.1 | 0.1 |
| Irganox 1010* antioxidant | 0 | 0.05 | 0 | 0 | 0.1 | 0 | 0 | 0.05 | 0.1 | 0.1 | 0 | 0 | 0 |
| Garbefix OS 240** phosphite | 0 | 0 | 0.1 | 0 | 0 | 0.2 | 0 | 0.1 | 0.1 | 0.2 | 0.1 | 0.1 | 0.2 |
| HALS/DHP Example 1b | 0 | 0 | 0 | 0.05 | 0 | 0 | 0.1 | 0 | 0 | 0 | 0.05 | 0.1 | 0.1 |

*Irganox 1010 = pentaerythrityl 3-tetra(4-hydroxy-3,5-di-tert-butylphenyl)propionate
**Garbefix OS 240 = tris(2,4-di-tert-butylphenyl)phosphite

TABLE IX

| Composition | Stabilizers | Thermomechanical stability |
|---|---|---|
| a | none | 1 |
| b | Irganox 1010 | 1.1 |
| c | Garbefix OS 240 | 1.7 |

TABLE IX-continued

| Composition | Stabilizers | Thermomechanical stability |
|---|---|---|
| d | HALS/DHP Example 1b | 1.3 |
| e | Irganox 1010 | 1.6 |
| f | Garbefix OS 240 | 1.9 |
| g | HALS/DHP Example 1b | 2.2 |
| h | Irganox 1010 + Garbefix OS 240 | 1.6 |
| j | Irganox 1010 + Garbefix OS 240 | 2.4 |
| k | Irganox 1010 + Garbefix OS 240 | 2.5 |
| l | HALS/DHP Example 1b + Garbefix OS 240 | 2.3 |
| m | HALS/DHP Example 1b + Garbefix OS 240 | 2.3 |
| n | HALS/DHP Example 1b + Garbefix OS 240 | 2.4 |

EXAMPLE 17

Heat stabilization of VB 6511 B polypropylene (PP) marketed by the Neste company 4 mixtures of the following compositions were prepared separately:
(i) Polypropylene: 100 g
(ii) Irganox 1076 antioxidant: 0.05 g
(iii) Calcium stearate: 0.1 g
(iv) Stabilizer (see Table X): 0 or 0.15 g Each of these mixtures was homogenized for 5 min. in a fast blender.

Sheets were then prepared by blending for 5 min. on a roll mill at the temperature of 170° C.

The sheets obtained were then pressed in a Schwabentham press under the following conditions:
(a) Contact: 40 s at 220° C.
(b) Pressing: 2 min. under 2.1 MPa The plaques thus obtained had a thickness of 1 mm.

These plaques were then placed in a ventilated oven temperature of 150° C.

Thermal degradation of the polymer was determined by the appearance of microcracks resulting in embrittlement of the polymer.

TABLE X

| Stabilizer | Degradation time |
|---|---|
| none | 280 h |
| Tinuvin 770 | 475 h |
| HALS/DHP Ex. 1b | 475 h |
| HALS/DHP Ex. 3b | >700 h |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A 1,4-dihydropyridine compound having the formula (Ia) or (Ib):

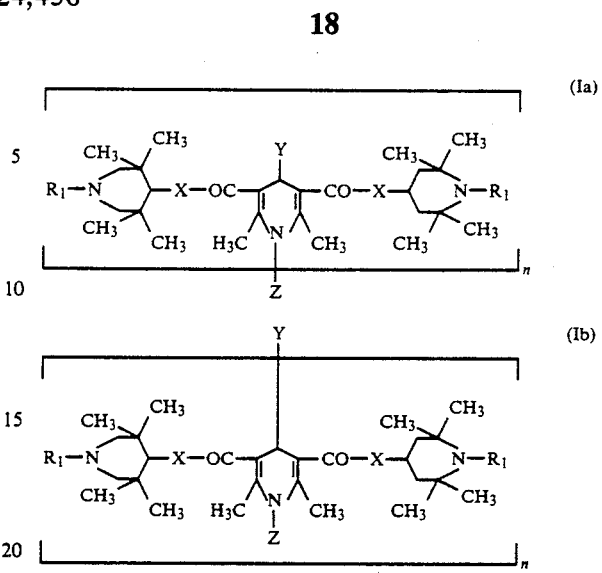

in which n is 1 or 2; $R_1$ is a hydrogen atom, a methyl radical or an acetyl radical; X is an oxygen atom or an $N-R_2$ radical wherein $R_2$ is a hydrogen atom or an alkyl radical having from 1 to 18 carbon atoms; Y is a hydrogen atom, an alkyl radical having from 1 to 18 carbon atoms or a phenyl radical; Z is a hydrogen atom or an alkyl radical having from 1 to 18 carbon atoms; with the proviso that, when n=2, one of the symbols Y and Z may be an alkylene radical having from 1 to 12 carbon atoms.

2. A dihydropyridine compound as defined by claim 1, having the formula (Ia).

3. A dihydropyridine compound as defined by claim 1, having the formula (Ib).

4. A dihydropyridine compound as defined by claim 1, wherein X is an oxygen atom.

5. A dihydropyridine compound as defined by claim 1, wherein X is an $N-R_2$ radical.

6. A dihydropyridine compound as defined by claim 1, wherein $R_1$ is a methyl radical.

7. A dihydropyridine compound as defined by claim 1, wherein Z is an alkyl radical having from 1 to 18 carbon atoms.

8. A dihydropyridine compound as defined by claim 1, wherein n is 1.

9. A dihydropyridine compound as defined by claim 1, wherein n is 2.

10. A dihydropyridine compound as defined by claim 1, being 2,6-dimethyl-3,5-bis[(1,2,2,6,6-pentamethyl-4-piperidyl)oxycarbonyl]-1,4-dihydropyridine.

11. A dihydropyridine compound as defined by claim 1, being 2,6-dimethyl-3,5-bis[(2,2,6,6-tetramethyl-4-piperidyl)oxycarbonyl]-1,4-dihydropyridine.

12. A dihydropyridine compound as defined by claim 1, being 2,6-dimethyl-3,5-bis[(2,2,6,6-tetramethyl-4-piperidyl)aminocarbonyl]-1,4-dihydropyridine.

13. A dihydropyridine compound as defined by claim 1, being 2,6-dimethyl-3,5-bis[(2,2,6,6-tetramethyl-4-piperidyl)-N-butylaminocarbonyl]-1,4-dihydropyridine.

14. A dihydropyridine compound as defined by claim 1, being 1,6-bis[2,6-dimethyl-3,5-bis[(1,2,2,6,6-pentamethyl-4-piperidyl)oxycarbonyl]-1,4-dihydro-4-pyridyl]hexane.

* * * * *